US00PP33474P2

(12) United States Plant Patent
Goffreda et al.

(10) Patent No.: US PP33,474 P2
(45) Date of Patent: Sep. 14, 2021

(54) PEACH TREE NAMED 'NJ361'

(50) Latin Name: ***Prunus persica* L.**
Varietal Denomination: NJ361

(71) Applicant: RUTGERS, THE STATE UNIVERSITY OF NEW JERSEY, New Brunswick, NJ (US)

(72) Inventors: Joseph C. Goffreda, Columbus, NJ (US); Anna M. Voordeckers, East Windsor, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 17/091,108

(22) Filed: Nov. 6, 2020

(51) Int. Cl.
*A01H 5/08* (2018.01)
*A01H 6/74* (2018.01)

(52) U.S. Cl.
USPC ..... Plt./197

(58) Field of Classification Search
USPC ..... Plt./197
See application file for complete search history.

*Primary Examiner* — Annette H Para
(74) *Attorney, Agent, or Firm* — Patrick J. Daugherty; Daugherty & Del Zoppo Co., LPA

(57) ABSTRACT

A new and distinct peach variety of *Prunus persica* named 'NJ361' is provided. This variety is distinguished from other peach varieties by its unique combination of showy flowers, medium to large, round, semi-freestone fruit, with a red to greyed-purple blush over a unique bright yellow-orange ground, ripening in mid-season, and possessing aromatic, sweet, acidic flavor.

6 Drawing Sheets

STATEMENT REGARDING FEDERALLY SPONSORED RESEARCH OR DEVELOPMENT

This invention was made with government support under contract or grant Multistate Research Project NE-9, entitled "Conservation and Utilization of Plant Genetic Resources," awarded or sponsored by the National Institute of Food and Agriculture. The government has certain rights in the invention.

Latin name of genus and species of the plant claimed: *Prunus persica* L.

Variety denomination: 'NJ361'.

BACKGROUND OF THE INVENTION

The present invention relates to a new and distinct variety of peach tree named 'NJ361' that resulted from crossing 'P.F. 23' (U.S. Plant Pat. No. 8,164) as the seed parent with peach seedling selection 'D91-184-94229' (non-patented). The new variety differs from seed parent 'P.F. 23' (U.S. Plant Pat. No. 8,164) in that the new variety ripen approximately two to three weeks earlier, has fruit with a bright, yellow-orange ground color, that retain their firmness for an extended period on the tree. The new variety differs from pollen parent 'D91-184-94229' in that the new variety ripens about one week earlier, produces fruit that better retain their firmness and do not have a propensity for the pits to split. The resulting tree was selected when growing in a cultivated area as the $44^{th}$ tree in the $38^{th}$ row of Block H at a fruit research farm in Cream Ridge, N.J.

BRIEF SUMMARY OF THE INVENTION

'NJ361' differs from the related cultivar 'Harken' (non-patented), in that fruit of 'NJ361' have fruit have a more unique yellow-orange ground color that is relatively more attractive. The 'NJ361' variety is also distinguished from other peach varieties due to the following unique combination of characteristics:

Produces medium to large, nearly round, semi-freestone fruit with a low tendency to split when adequately cropped.

Fruit have an attractive red to greyed-purple blush over a unique bright, yellow-orange ground color.

Excellent production of firm fruit that ripen in mid-season on trees with low to medium susceptibility to bacterial leaf spot.

Fruit have preferable eating quality due to their sweet and acidic flavor.

The variety was asexually reproduced at a fruit research farm in Cream Ridge, N.J. Asexual reproduction of this new variety by budding onto >Lovell=peach seedling rootstock (non-patented) shows that the foregoing characteristics are so reproduced.

The following detailed description concerns the original tree, 'NJ361'. The original tree and asexual progeny have been observed growing in a cultivated area at a fruit research farm in Cream Ridge, N.J. Certain characteristics of this variety, such as growth and color, may change with changing environmental conditions (such as, light, temperature, moisture, nutrient availability) or other factors. Color descriptions and other terminology are used in accordance with their ordinary dictionary descriptions unless the context clearly indicates otherwise. Color designations are made with reference to *The Royal Horticultural Society* (*R.H.S.*) *Colour Chart* (1966 Ed.)

BRIEF DESCRIPTION OF THE DRAWINGS

This new variety is illustrated by the accompanying photographic drawings of the 'NJ361' plant at approximately seven (7) years old, depicting the peach tree by the best possible color representation using color photography. Colors are approximate as color depends on horticultural practices, such as light level, fertilization rate, and other conditions and, therefore, the color characteristics of this new variety should be determined with reference to the observations described herein, rather than from these illustrations alone.

Figure 1:
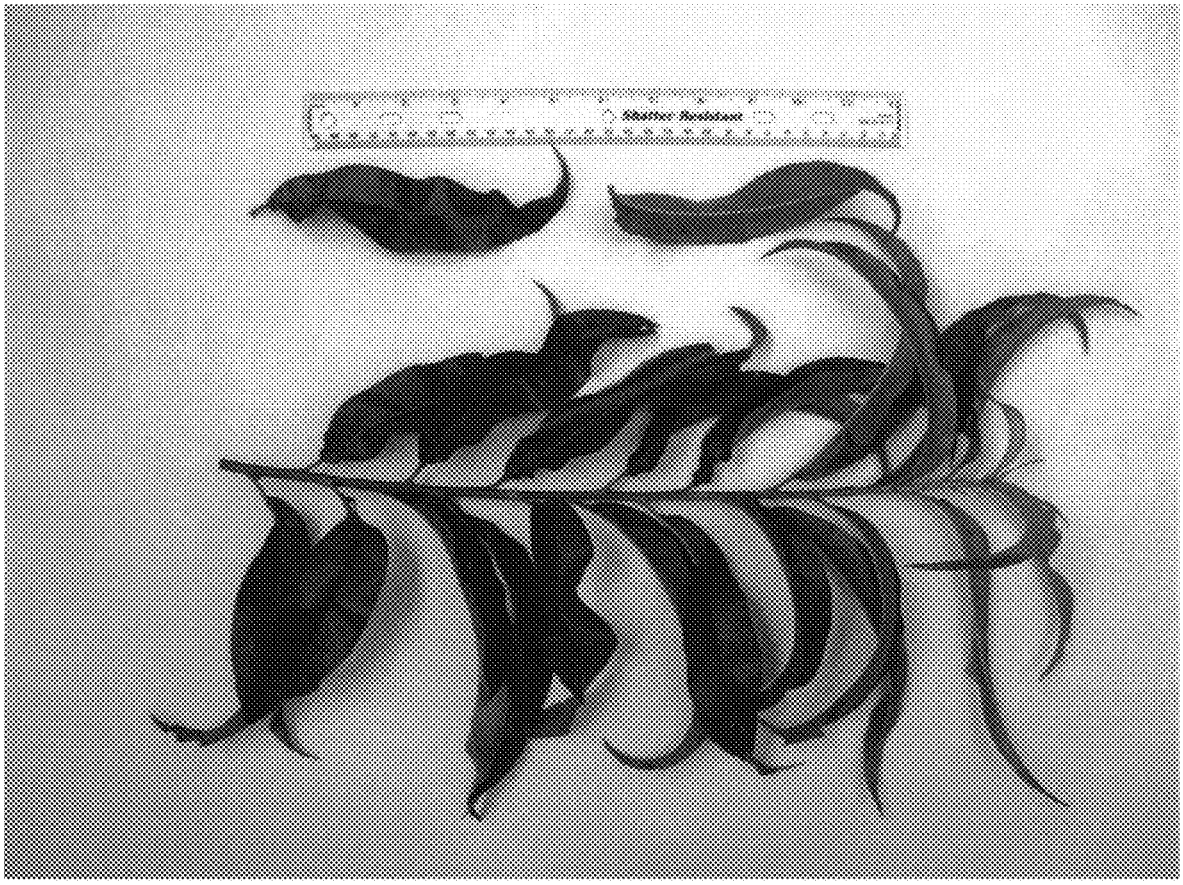
FIG. 1 is a color photograph taken on Aug. 12, 2019 of a characteristic twig of 'NJ361' in mid-summer bearing typical leaves of the foliage.
Figure 2:
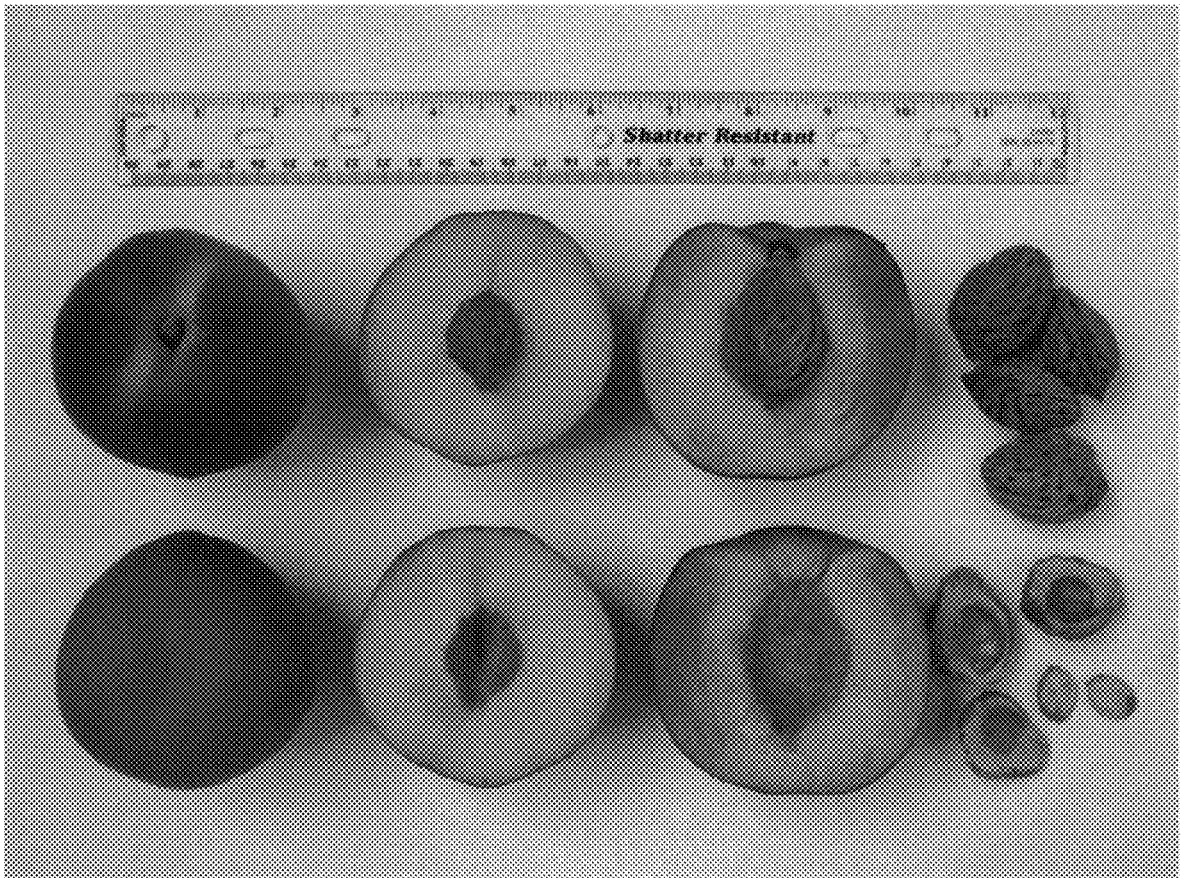
FIG. 2 is a color photograph taken on Jul. 29, 2019 of characteristic mature fruit and stones of 'NJ361'. Whole fruit are presented in two positions and both a transverse and longitudinal cross section to illustrate that the pericarp partially adheres to the pit when the fruit is mature. The stones exemplify the obovate shape and pits and grooves on the surface of the stone.
Figure 3:
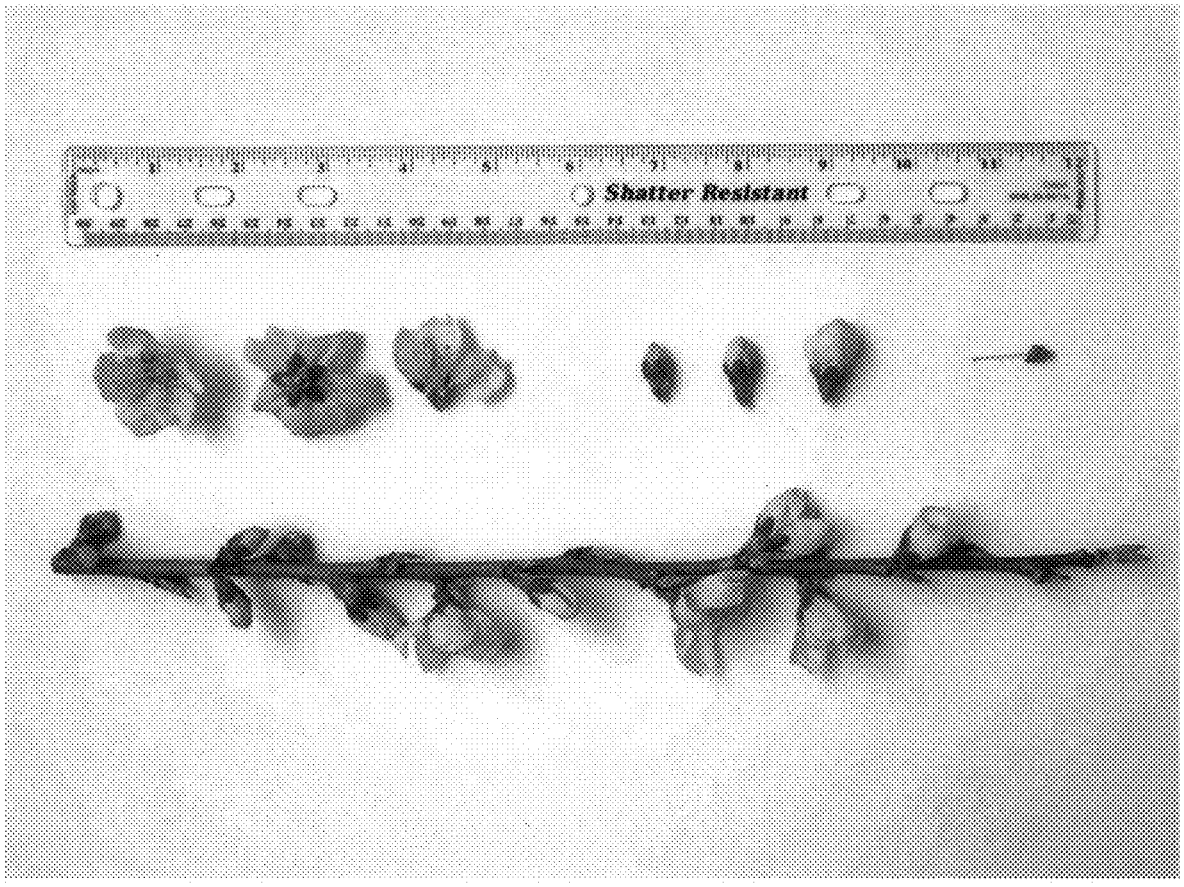
FIG. 3 is a color photograph of a characteristic twig that illustrates the typical flower buds and large, showy flowers of 'NJ361' observed on a tree at a fruit research farm in Cream Ridge, N.J. on Apr. 9, 2019.
Figure 4:
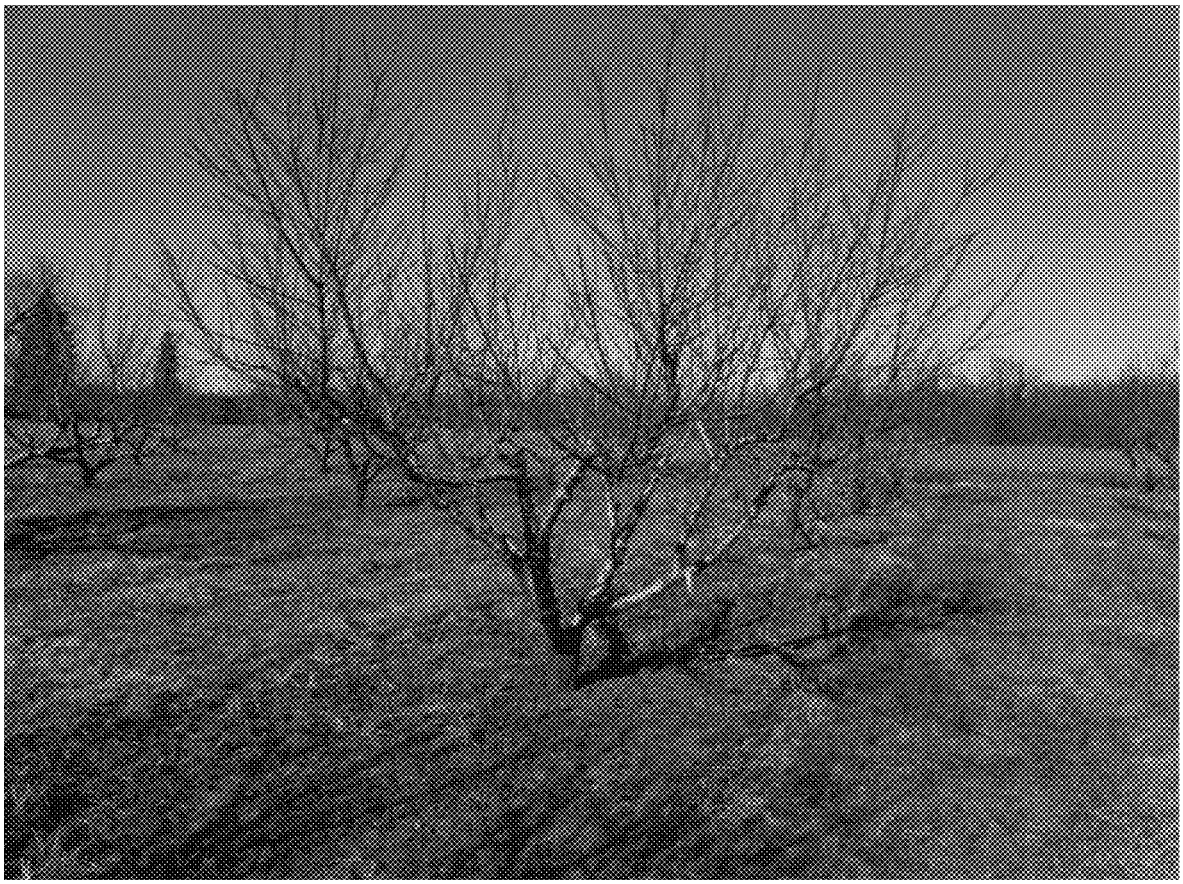
FIG. 4 is a color photograph of a dormant tree of 'NJ361', prior to pruning, in early spring that illustrates the spreading growth habit of a tree at the fruit research farm in Cream Ridge, N.J. on Mar. 26, 2019.
Figure 5:
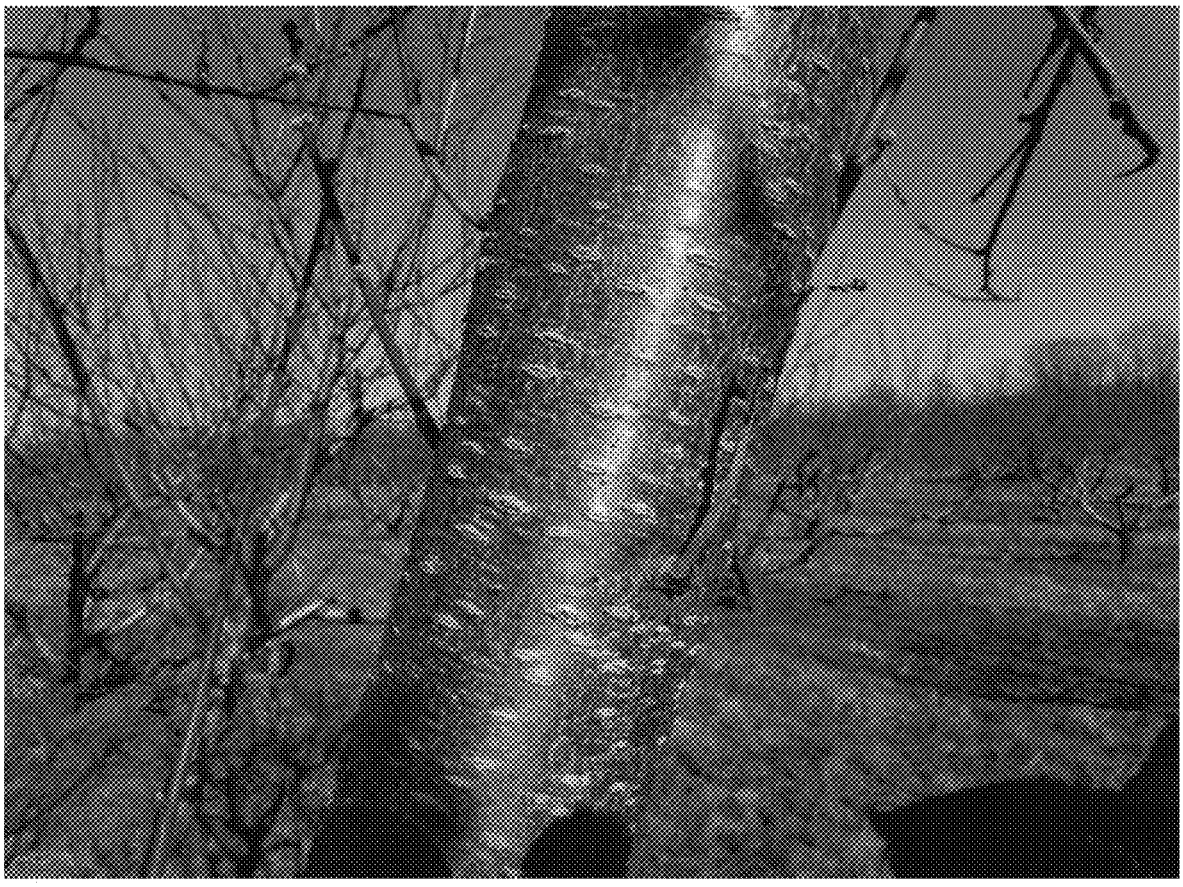
FIG. 5 is a color photograph taken on Sep. 26, 2019 of immature bark of 'NJ361' that illustrates color and the moderate density of conspicuous elliptic lenticels on the immature bark.
Figure 6:
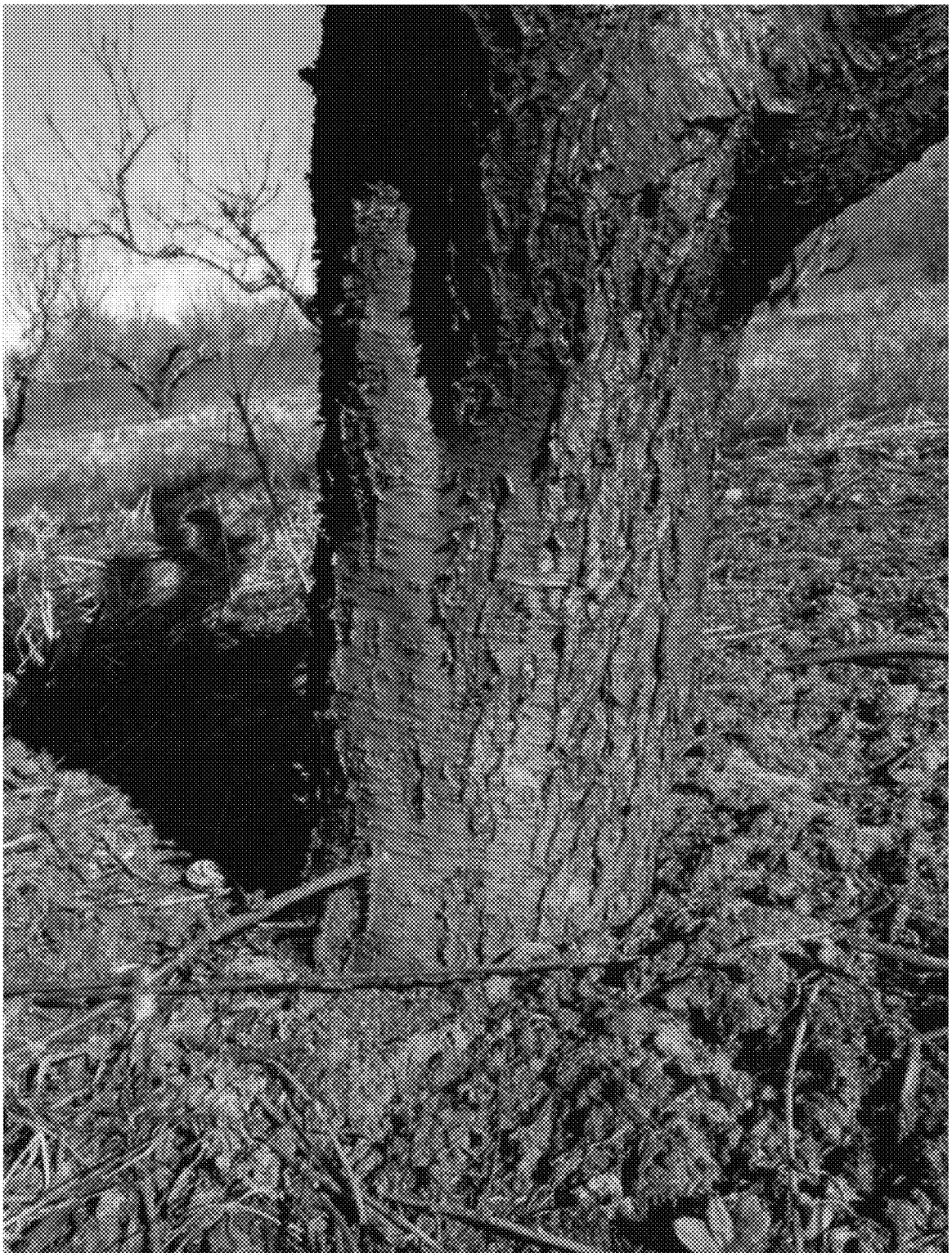
FIG. 6 is a color photograph taken on Sep. 26, 2019 of mature bark of 'NJ361' that illustrates the greyed-green color, moderately rough texture, with several broad, shallow furrows on the mature bark.

The colors of and illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'NJ361' variety is based on observations of an asexually reproduced tree. The observed tree was seven years of age and growing on 'Lovell' seedling rootstock (non-patented) at the fruit research farm in Cream Ridge, N.J.

Scientific name: *Prunus persica* L.

Parentage:

*Seed parent*.—'P.F. 23'.

*Pollen parent*.—'D91-184-94229'.

Tree:

*Vigor*.—Vigorous.

*Plant hardiness zone*.—Growth of plants has only been observed in zone 6b.

*Dormant flower bud cold tolerance*.—At least to −21° C.

*Leaf bud burst*.—Typically in mid-April when grown in Cream Ridge, N.J., but can vary by one to two weeks.

*Overall shape*.—Spreading.

*Height*.—Average as compared to other peach cultivars. For example, measurement of a typical grafted tree on 'Lovell' peach seedling rootstock (non-patented) at seven years after planting shows an average height of 3.4 meters when grown in Cream Ridge, N.J.

*Width*.—Average as compared to other peach cultivars. For example, measurement of a typical grafted tree on 'Lovell' peach seedling rootstock (non-patented) at seven years after planting shows an average width of 4.6 meters when grown in Cream Ridge, N.J.

*Caliper*.—Seven-year-old tree is 62 cm. in circumference measured at 20 cm. from the ground.

Trunk and branches:

*Trunk bark texture*.—Moderately rough, with several, broad, shallow furrows.

*Trunk bark color*.—Greyed-green (between RHS 197C and RHS 197D).

*Primary branches*.—Branches that are approximately 15 cm. in circumference are greyed-green (RHS 176C) overlaid with grey (between RHS 201B and RHS 201C).

*Lenticels*.—Moderate density, approximately 0.9 per square cm; elliptical in shape and conspicuous; typical examples of which averaged 4.7 mm. in length and 2.1 mm. in width; greyed-green (RHS 198D) in color becoming greyed-orange (between RHS 169C and RHS 169D) towards the center.

*Branch pubescence*.—None.

*New growth bark*.—Greyed-purple (between RHS 184B and RHS 184C) in sun; yellow-green (RHS 145A) in shade.

*Internodes*.—Length averaging 18.8 mm. on a one-year shoot.

Leaves:

*Texture*.—Glabrous, both surfaces.

*Sheen*.—Young leaves satin to semi-glossy to nearly flat, with a flat finish on the underside.

*Length*.—About 145 mm. to 180 mm., averaging about 167 mm. including the petiole.

*Width*.—About 35 mm. to 42 mm., averaging about 40 mm.

*Petiole*.—Averaging 12.2 mm. long and about 1.9 mm. in diameter; Color: Yellow-green (146 C).

*Margin*.—Crenate.

*Margin undulation*.—Typically slight.

*Form*.—Lanceolate, and concave in cross section.

*Apex*.—Acuminate, curved downward.

*Base*.—Broadly acute.

*Venation*.—Pinnate.

*Glands*.—

*Number*.—Typically between 2 to 5, averaging about 3.9.

*Position*.—Nearly equally distributed on the leaf and petiole.

*Size*.—Length averaging 1.3 mm. and width averaging 1.1 mm.

*Form*.—Reniform.

*Stipules*.—Stipules are present on immature leaves, but they are not persistent. Typically, there are two per immature leaf, with an average length of about 12 mm. The color is yellow-green (between RHS 146A and RHS 146B), becoming red-purple (RHS 59A) just prior to dehiscence. None observed on mature leaves.

*Leaf color*.—

*Upper leaf surface*.—Green (between RHS 137A and RHS 137B).

*Lower leaf surface*.—Yellow-green (RHS 146B).

*Vein*.—Yellow-green (RHS 151B).

*Pubescence*.—None.

Flowers:

*Size*.—Large size, typical flower measuring between 36 mm. and 42 mm, averaging about 39 mm across.

*Color*.—

*Dormant bud*.—Grey (RHS 201C) becoming grey (RHS 201A) near the base.

*Pink stage bud*.—Red-purple (between RHS 62A and RHS 62B).

*Open flower*.—Freshly open flowers are red-purple (RHS 62D) becoming red (between RHS 55B and RHS 55D).

*Petals*.—Typically five petals per flower; slightly cupped, nearly round, with slight undulation on some petals, averaging about 20 mm. long and 18 mm. wide.

*Petal apex*.—Obtuse, nearly rounded.

*Petal base*.—Cuneate.

*Stamens*.—

*Number*.—Generally 45.

*Position*.—Perigynous and near the point of attachment of the petals.

*Length*.—Variable, between 6 mm. to 12 mm, averaging 9.6 mm.

*Filament color*.—Red-purple (RHS 73D) becoming red-purple (RHS 73B) at petal fall.

*Anther color*.—Adaxial and abaxial surface is greyed-red (RHS 182A).

*Stigma*.—Located slightly above most of the stamens.

*Pistil*.—

*Number*.—One.

*Size*.—Length between 18 and 23 mm., averaging 21 mm.

*Pistil color*.—Yellow-green (RHS 145B).

*Ovary*.—Light, short pubescence less than 0.5 mm in length and ellipsoid in shape, color yellow-green (RHS 145A).

*Sepals*.—

*Number*.—Five.

*Pubescence*.—Length short, less than 1 mm., low to moderate density.

*Color*.—Greyed-purple (between RHS 183A and RHS 183B) over a yellow-green (RHS 145A) ground color.

*Shape*.—Triangular, with a rounded apex.

*Size*.—Length averaging 5.7 mm., width averaging 4.2 mm.

*Nectar cup color*.—Orange (RHS 28B).

*Pollen*.—Abundant, viable and plant is typically self-fruitful; Color is greyed-yellow (RHS 162A).

*Fragrance*.—Nearly none.

*Bloom season*.—Onset of bloom at Cream Ridge, N.J. in 2019 on April 6; full bloom on April 12.

Fruit:

*Size*.—Medium to large, averaging about 7.1 cm. long, 7.4 cm. wide parallel to the suture and 7.3 cm. wide perpendicular to the suture.

*Typical weight*.—Between 180 to 280 g, averaging about 210 g.

*Form*.—

*Longitudinal section*.—Nearly round.

*Traverse section*.—Nearly round.

*Suture*.—Very shallow, extending from base to apex.

*Ventral surface*.—Nearly smooth.

*Base*.—Generally flat.

*Apex*.—Flat; apex tip is a small point.

*Stem*.—Average length of 7.9 mm. and an average diameter of 3.7 mm.

*Skin*.—

*Thickness*.—Medium, yet resilient.

*Surface*.—Pubescent, moderate density and very short, typically less than 0.5 mm.

*Tenacity*.—Medium.

*Astringency*.—None.

*Tendency to crack*.—Low.

*Color*.—Blush is red (RHS 46A) in partial sun; greyed-purple (RHS 185A) in full sun; ground color is yellow-orange (between RHS 23B and RHS 23C).

*Fruit properties*.—

*Flesh color*.—Yellow-orange (between RHS 16B and RHS 16C), with red (RHS 46A) near the skin of some fruit.

*Flesh firmness*.—Above average.

*Flesh adhesion*.—Semi-freestone.

*Juice*.—Moderate.

*Texture*.—Firm but melting.

*Fibers*.—Not noticeable.

*Ripens*.—Between July 28 and August 12 at Cream Ridge, N.J.

*Flavor*.—Sweet, acidic.

*Soluble solids*.—14.9%.

*Aroma*.—Slight to moderate.

*Eating quality*.—Very good.

*Keeping quality*.—Medium. Has held its flavor and firmness for at least 14 days in cold storage at 1° C. to 2° C.

*Shipping quality*.—Good. No bruising or scaring disorders have been observed.

*Usage*.—Dessert.

*Market*.—Local and long distance.

*Productivity*.—Very good, though varies greatly depending upon conditions inclusive of winter and spring temperatures, rainfall, tree density, pruning methods, soil type, fertilization, irrigation, and degree of fruit thinning. Trees have produced a full crop in 7 out of 10 years in Cream Ridge, N.J.

Stone:

*Type*.—Semi-freestone.

*Form*.—Generally obovate.

*Base*.—Medium.

*Apex*.—Wide.

*Surface*.—Pits and grooves.

*Ventral suture*.—Medium to large.

*Dorsal ridge*.—Medium height, medium width, forming medium-deep lines.

*External color*.—Greyed-orange (between RHS 165C and RHS 165D), sometimes overlaid with greyed-red (between RHS 182A and RHS 182B).

*Cavity surface color*.—Greyed-orange (between RHS 165C and RHS 165D).

*Average stone dry weight*.—7.5 g.

*Average stone wall thickness*.—Varies between 5.1 mm. along the dorsal ridge to 12.7 mm at the base.

*Size*.—Averages about 37.5 mm. long, 28 mm. wide parallel to the dorsal ridge, and 22.7 mm wide perpendicular to the dorsal ridge.

*Tendency to split*.—Typically low.

Kernel:

*Dry weight*.—0.13 g.

*Form*.—Variable. Irregular elliptic to elliptic.

*Skin color*.—Greyed-orange (RHS 165B).

*Vein color*.—Greyed-orange (between RHS 164A and 165B).

*Viability*.—Inviable.

*Size*.—Averages about 17.7 mm. long, 10.4 mm. wide, and 1.3 mm. in breadth.

*Plant/fruit disease and pest resistance/susceptibility*.—No atypical resistances/susceptibilities have been noted under normal cultural practices.

We claim:

1. A new and distinct variety of peach tree, substantially as herein shown and described.

* * * * *